United States Patent
Lin

[11] Patent Number: 5,919,139
[45] Date of Patent: Jul. 6, 1999

[54] VIBRATIONAL DOPPLER ULTRASONIC IMAGING

[75] Inventor: Gregory Sharat Lin, Fremont, Calif.

[73] Assignee: Diasonics Ultrasound, Santa Clara, Calif.

[21] Appl. No.: 08/993,337

[22] Filed: Dec. 19, 1997

[51] Int. Cl.[6] .................................................. A61B 8/00
[52] U.S. Cl. .......................................................... 600/443
[58] Field of Search .................................. 600/443, 444, 600/447, 448, 449; 128/916

[56] References Cited

U.S. PATENT DOCUMENTS

5,694,937  12/1997  Kamiyama ............................. 600/443

*Primary Examiner*—Marvin M. Lateef
*Assistant Examiner*—Maulin Patel
*Attorney, Agent, or Firm*—Blakely, Sokoloff, Taylor & Zafman LLP

[57] ABSTRACT

A system is disclosed for performing vibrational Doppler ultrasonic imaging. A vibrational wave of a first frequency is introduced into an area of a subject to be scanned. An ultrasound signal is simultaneously introduced into the area. The vibrational wave is of a sufficient frequency and amplitude to induce palpable vibrations in the tissue medium of the area being scanned. An ultrasonic Doppler imaging system detects these tissue vibrations and processes the resulting scanned data for display on a display device.

22 Claims, 8 Drawing Sheets

VIBRATIONAL DOPPLER ULTRASONIC IMAGING

FIELD OF THE INVENTION

The present invention relates generally to medical devices, and more specifically to ultrasonic imaging using an audio frequency vibrational source.

BACKGROUND OF THE INVENTION

Ultrasonic imaging technology has become a vital tool for examining the internal structure of living organisms. For the diagnosis of various medical conditions, ultrasonic imaging is often useful to examine soft tissues within the body to show the structural detail of internal tissues and fluid flow.

To examine internal body structures, ultrasonic images are formed by producing very short pulses of ultrasound using a transducer, sending the pulses through the body, and measuring the properties of the echoes (e.g., amplitude and phase) from tissues within the body. Typically, the ultrasound beam is focused at various steps within the body to improve resolution or image quality. Echoes are received by the transducer and processed to generate an image of the object. The resulting image is usually referred to as a B-scan image.

Measuring and imaging blood (and other bodily fluid) flow within a living subject is typically done using the Doppler principle, wherein a transmitted burst of ultrasound at a specific frequency is reflected from moving blood cells, thereby changing the frequency of the reflected ultrasound in accordance with the velocity in the direction of the flow. The frequency shift (Doppler shift) of reflected signals with respect to the transmitted signals is proportional to the velocity of the fluid flow. This frequency may be detected and displayed on a video display to provide graphic images of moving tissue structure and fluid flow within a living patient.

Present ultrasound techniques include frequency-shift color Doppler and power color Doppler imaging of tissue motion, as well as the cross-correlation ultrasound estimation of displacements and mean velocities for color mapping tissue motion (referred to as CVI and developed by Philips Corp.). Another known technique is the single or multi-compression cross correlation ultrasound elastography method using radio frequency (RF) signals.

Present known methods of ultrasound tissue imaging using color Doppler techniques and cross-correlation exhibit relatively poor signal-to-noise ratios because small displacement, low-velocity tissue motions are relatively close to the noise floor. The multi-compression, cross-correlation approach requires radio frequency data and is very computationally intensive, presently requiring non-real time, off-line processing.

These present ultrasound methods are directed toward estimating the direction and velocity of fluid flow within a body, and are therefore not optimized for detecting and measuring certain mechanical properties of the tissue being scanned. The mechanical properties not adequately detected by present ultrasound methods include elasticity, inertia, resonance, and damping characteristics of tissue media. An accurate evaluation of these mechanical properties of soft tissue within a subject can contribute greatly to understanding the condition and identity of the tissues and structures being scanned.

However, because these mechanical properties exhibit only a small measure of vibrational motion relative to typical fluid flow within a body, adequate detection requires devices which are more sensitive than existing systems. Although certain elastographic imaging systems exist, they involve complex circuitry and do not provide real-time analysis.

It is therefore an intended advantage of the present invention to provide a device which performs Doppler sonography of small displacement, low-velocity tissue motion with increased signal-to-noise ratio in the Doppler signal path.

It is a further intended advantage of the present invention to provide a an ultrasound device which performs real-time analysis of certain mechanical properties of tissue.

It is yet a further intended advantage to provide a method of performing elastographic imaging using existing ultrasound systems and a relatively simple and easy to use attachment device.

SUMMARY OF THE INVENTION

An ultrasonic imaging device using an audio frequency vibrational source is disclosed. A first transducer transmits vibrational energy of a first frequency into an area of a subject to be scanned. An ultrasound transducer transmits ultrasound pulses into the area. The vibrational energy transmitted by the first transducer induces palpable vibrations in the tissue medium of the area being scanned. The amplitude and frequency variance of these vibrations reflect certain mechanical properties, such as elasticity, inertia, resonance, and vibration damping properties of the tissue.

In one embodiment of the present invention, the first transducer includes an audio speaker and is connected to a variable frequency tone generator that produces audio waveforms which are converted to vibrational energy by the speaker. The audio transducer and ultrasound transducer are coupled to each other through a duplex probe bracket which holds both transducers and allows the audio transducer to be pivoted relative to the ultrasound transducer. An ultrasonic color Doppler imaging system connected to the ultrasound transducer processes the received imaging data from the ultrasound probe for display on a video monitor. The imaging system combines amplitude and variance data to generate a signal indicative of the magnitude and frequency variability of the vibrations induced by the audio transducer.

Other features of the present invention will be apparent from the accompanying drawings and from the detailed description which follows.

BRIEF DESCRIPTION OF THE DRAWINGS

The present invention is illustrated by way of example and not limitation in the figures of the accompanying drawings, in which like references indicate similar elements, and in which.

DETAILED DESCRIPTION

A system is described for performing real-time ultrasonic imaging of the spatial distribution of elastic, inertial, vibrational resonance, and vibrational damping properties in heterogeneous compressible media, including soft biological tissue. The system utilizes the fact that Doppler frequency shifts, amplitudes, and variances are significantly larger under induced vibration than in unperturbed media or tissue. The system uses a consistent, controllable, and reproducible sub-ultrasound frequency vibration which is introduced into tissue to be scanned by Doppler ultrasound imaging techniques. The ultrasound and sub-ultrasound vibrations are introduced simultaneously into the tissue, and the resulting Doppler data is measured and displayed.

In the following description, numerous specific details are set forth in order to provide a thorough understanding of the present invention. However, it will be understood by those skilled in the art that the present invention may be practiced without these specific details.

Various embodiments of the present invention may be implemented in discrete hardware components or, alternatively, in programmed processing units such as digital signal processors using software which is compiled, linked and then loaded from disk-based storage for execution during run-time. Various programs containing the methods employed in these embodiments may also reside in firmware or other similar nonvolatile storage means.

Figure 1:
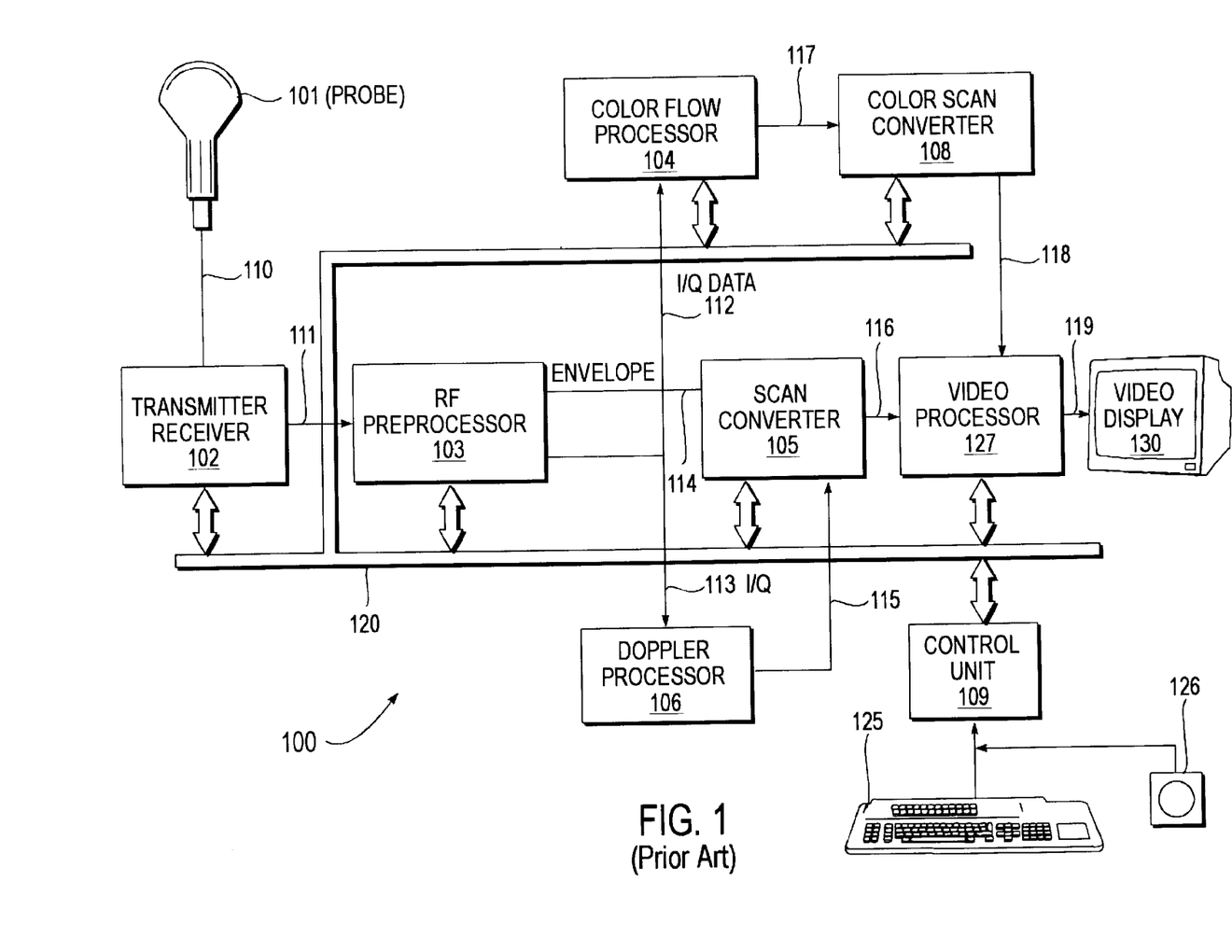
FIG. 1 is a block diagram of a prior art ultrasonic imaging device.

FIG. 1 illustrates a typical prior art ultrasonic imaging system, shown as imaging system 100. Imaging system 100 generally comprises a probe 101, which is typically a multi-element array of piezoelectric elements which both send and receive ultrasound signals when examining a subject, such as a living patient. Probe 101 is coupled via signal path 110 to transmitter/receiver circuitry 102, which is designed according to principles well known in the ultrasound imaging art, and which, for purposes of brevity, will not be discussed in further detail.

Transmitter/receiver circuitry 102 is coupled to a control unit 109 via bus 120 and is controlled so that the elements in probe 101 are focused at particular points in the body during both transmission and reception of ultrasound signals. Transmitter/receiver circuitry 102 and control unit 109 also often provide a scanning function so that a two-dimensional image may be generated without moving probe 101 with respect to the body.

Following transmission of ultrasound signals into the body, reflected signals are processed by a receiver (known as a "beam former") in transmitter/receiver circuitry 102. The multitude of signals from each individual element of probe 101 is converted into a single signal which is sent to RF (Radio Frequency) processor 103 via signal path 111.

RF processor 103 processes the signal information to produce a demodulated and unipolar envelope signal and in-phase (I) and quadrature (Q) Doppler signals. The envelope signal represents the amplitude of echoes returning from the body and is further transmitted via signal path 114 to a scan converter 105 which is a typically a large digital electronic memory.

Scan converter 105 stores the envelope echo information on a line-by-line basis together with the geometrical position of such information in the body resulting from the scanning process, in such a manner that a two-dimensional video image may be constructed and transmitted to video processor 127 via signal path 116.

In the absence of any color Doppler information, video processor 127 simply sends a conventional video signal over signal path 119 to video display monitor 130. This two-dimensional image, usually black and white, represents the distribution of echo generating sites within the body. The so-called B-scan image is then used by the operator to search the body for pathology or by the physician in developing a diagnosis.

I and Q signals for so-called single-gate Doppler are sent to Doppler processor 106 via signal path 113. Doppler processor 106, under the control of control unit 109 via bus 120, compares signals from several successive echoes to determine the Doppler shift in a single region in the body which is commonly known as the sample volume. Doppler processor 106 also produces a continuous time series of spectral Doppler information in which blood flow velocities are displayed in black and white on video display 130 over one or more cardiac cycles (typically several seconds), having first been sent to scan converter 105 via signal path 115, to video processor 127 via signal path 116 and to video display 130 via signal path 119.

RF processor 103 transmits I and Q signals via signal path 112 to color flow processor 104. Color flow processor 104 typically processes several sample volumes along a given scanning direction in the body. Color flow processor passes signals to color scan converter 108 via signal path 117 where, in a manner similar to the black and white scan converter 105, color encoded signals are stored on a line-by-line basis, together with the geometrical position of such information in the body resulting from the scanning process, in such a manner that a two-dimensional color video image may be constructed and transmitted to video processor 127 via signal path 118.

Color scan converter 108, which may also be used to interpolate scan line information obtained from color flow processor 104, then transmits color Doppler information via signal path 118 to video processor 127 for display on video display 130. Video processor 127 typically includes decision circuits to choose whether a given specific part of the two dimensional image has color information resulting from flow or whether it only has echo information from static tissue. If flow is present, the color information is displayed at the correct point in the image rather than the black and white image information.

Vibrational Doppler Imaging

In one embodiment of the present invention, the ultrasonic imaging system 100 of FIG. 1 is used in conjunction with a device which introduces vibrations at a sub-ultrasonic (audio) frequency into the scanned subject simultaneously with the ultrasound waves introduced by an ultrasound probe.

In a method of the present invention, an audio-frequency tone is introduced into the medium or tissue to be scanned. The tone is of sufficient amplitude to induce palpable vibrations in the medium or tissue to be scanned, and can be detected by a conventional ultrasonic color Doppler imaging apparatus. Doppler signal processing is modified to reduce gain, discard frequency-shift data, and combine amplitude and/or variance data to generate a signal indicative of the magnitude and velocity range of the vibrations. This data is mapped according to a gray or color scale into two-dimensional image space.

When an audio-frequency vibrational source is applied to the surface of a compressible medium (such as soft biological tissues), it initiates traveling longitudinal waves radiating from the point of contact. Any given volume element of the medium undergoes alternating compression and rarefaction (strain displacements) in response to the sinusoidal stresses of the traveling longitudinal wave. The magnitude of the strain displacements are a measure of the elasticity of that volume element. The magnitude can be calculated using Hooke's law:

$$p=Y\times(\Delta l/l).$$

In the above equation, p is the pressure (i.e., force per unit area) or stress exerted by the traveling longitudinal wave, $\Delta l/l$ is the stretch per unit length (i.e., fractional stretch) or strain, and Y is Young's modulus for that volume element of medium.

Because the vibrations are continuous wave, the frequency of the traveling longitudinal wave is fixed. By bouncing ultrasonic waves off of the medium, Doppler signal processing detects frequency shifts in the returning echoes from moving acoustic reflectors within each volume element of the medium. Whenever a frequency shift is detected above a given threshold magnitude (e.g., by a high-pass filter generally set just above the low-frequency noise floor), motion is detected. Because frequency shifts alternate between positive and negative Doppler shifts at the rate of vibration, the temporally-averaged frequency shift signal cancels itself out, leaving only noise. However, the amplitude and variance signals are measures of the fractional volume of acoustic reflectors exceeding the given threshold Doppler shift and the range of variability.

The amplitude is also proportional to the density and echogenicity of acoustic reflectors per volume element, and inversely related to attenuation in the intervening medium. Hence, a purely amplitude Doppler image of induced vibrations exhibits a "contaminating" echogenicity component in addition to the elastographic component. This echogenicity component can be minimized to a certain extent by rejecting certain low-strain, high-echogenicity signals with the high-pass filter. This component can be further minimized by adding or combining it with the variance signal. Without the echogenicity component, vibrational Doppler imaging could be called "Doppler elastography."

In one embodiment of the present invention, vibrational Doppler imaging (VDI) is accomplished by a duplex probe, consisting of an audio-frequency transducer (transmit only) attached side-by-side to a conventional ultrasonic transducer (transmit and receive).

Figure 2:
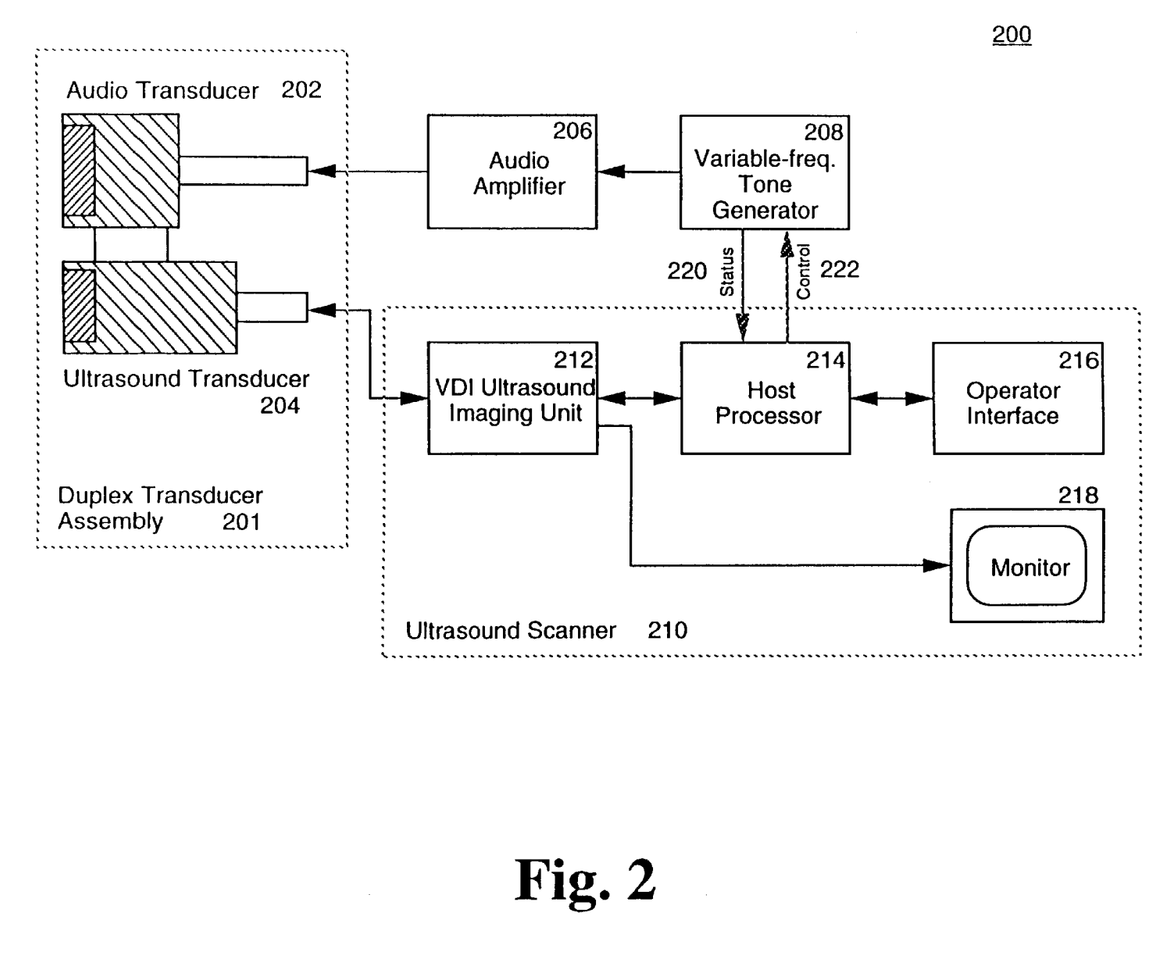
FIG. 2 is a block diagram of a vibrational ultrasonic imaging device according to one embodiment of the present invention.

FIG. 2 is a high level block diagram illustrating a vibrational Doppler imaging device according to one embodiment of the present invention. Vibrational Doppler imaging system 200 comprises an audio transducer 202 attached to an ultrasound transducer 204. Ultrasound transducer 204 can be a typical ultrasound probe, such as probe 101 illustrated in FIG. 1. Audio transducer 202 and ultrasound transducer 204 are arranged in a duplex transducer (or probe) assembly 201 which holds both probes together through vibrational insulation and accommodates one-handed use by an operator.

A variable-frequency, variable-waveform signal generator 208 supplies tone signals to an audio amplifier 206 which drives the audio transducer 202. The variable frequency signal generator 208 includes controls which allow a user to change various audio signal parameters, such as waveform shape and frequency. Audio amplifier 206 controls the amplitude of the signal generated by signal generator 208.

The ultrasound transducer 204 is connected to a Doppler ultrasound scanner 210. In one embodiment of the present invention, the ultrasound section of the vibrational Doppler imaging system 200 is a complete standard color Doppler ultrasound system, such as system 100 of FIG. 1. The ultrasound scanner 210 includes the processing and imaging units necessary to control the amplitude, variance, and combined mapping functions for the transmitted and received ultrasound signals.

Ultrasound scanner 210 includes Doppler ultrasound imaging unit 212 which provides control for amplitude, variance, and combined mapping of the transmitted and received ultrasound signals. Ultrasound imaging unit 210 is connected to a display monitor 218, which provides graphical output of color Doppler images processed by ultrasound imaging unit 212.

Ultrasound scanner 210 also includes a host processor 214. Ultrasound imaging unit 212 transmits image data and receives control signals from host processor 214. In one embodiment of the present invention, host processor 214 is also connected to the variable frequency tone generator 208 on the audio side of system 200. The host processor 214 receives status information over status line 220 from the variable frequency signal generator 208, and, in turn, sends control signals over control line 222 to signal generator 208. This allows an operator to control the audio signal frequency and amplitude produced by the variable frequency signal generator 208 through computer control, rather than through separate controls on the signal generator itself.

Operator control of the parameters for the signal generator and other processing functions performed by host processor 214 is provided by operator interface 216. Operator interface 216 may be embodied within a graphical user interface displayed on a monitor connected to host processor 214 through which the operator can set the audio parameters through numeric entry fields or graphical option buttons. Alternatively, operator interface 216 may be a hardwired interface to host processor 214 through which the operator enters audio signal parameters through switches or dials.

In an alternative embodiment of the present invention, host processor is not directly coupled to variable frequency tone generator 208 through status and control lines 220 and 222. In this embodiment, the operator controls the characteristics of the audio signals to be transmitted through audio transducer 202 through control knobs on audio amplifier 206 and signal generator 208.

Figure 3:
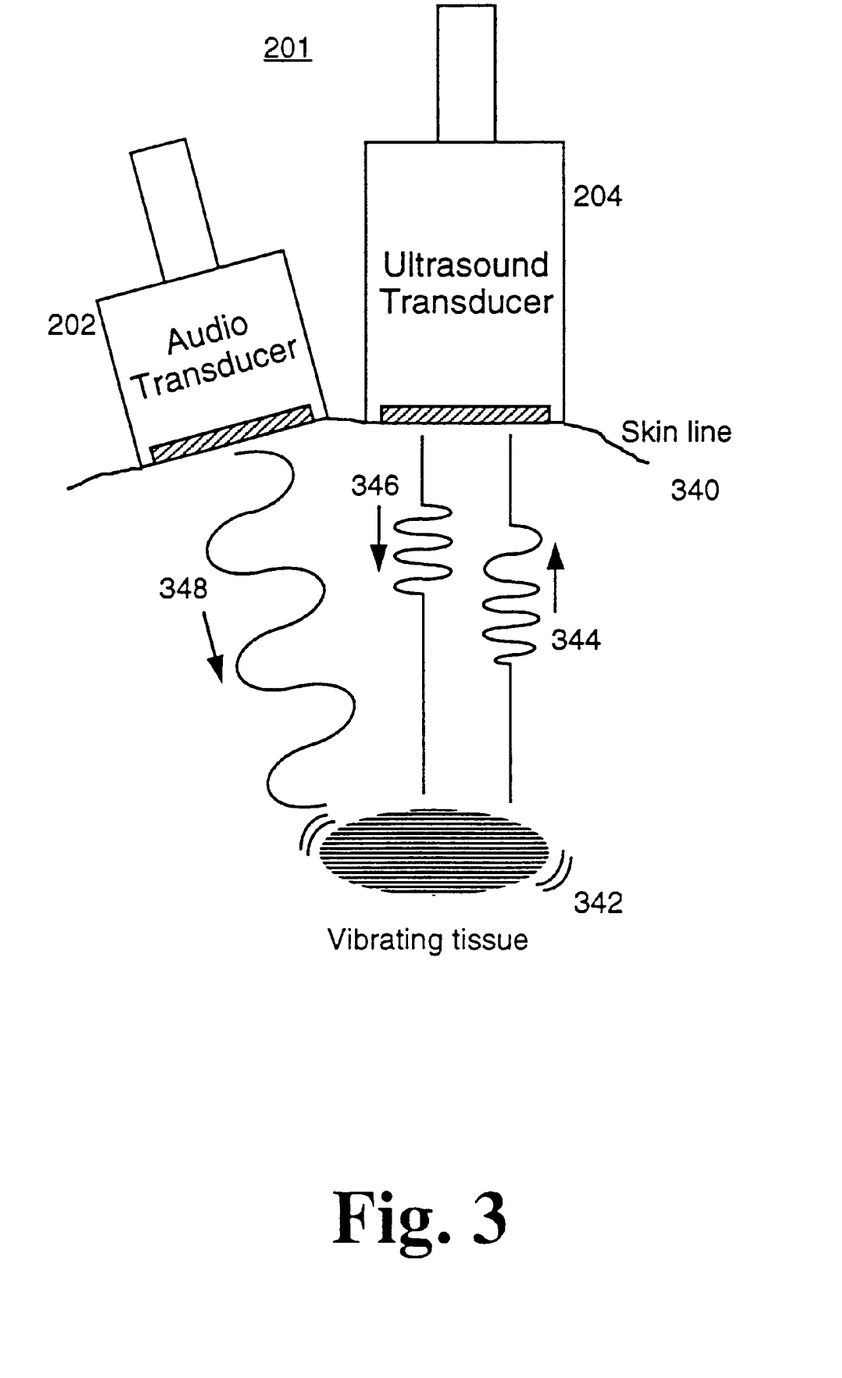
FIG. 3 illustrates the introduction of vibrational and ultrasound waves into a body according to one embodiment of the present invention.

FIG. 3 illustrates the introduction of audio-frequency vibrations in soft tissue during ultrasound imaging according to one embodiment of the present invention. FIG. 3 provides an example of how the duplex probe and VDI system 200 illustrated in FIG. 2 can be used to perform vibrational Doppler imaging on a patient according to a method of the present invention.

Duplex probe 201 includes audio transducer 202 and ultrasound transducer 204 which are both held against the skin 340 of the patient. In one embodiment of the present invention, the audio transducer 202 is held in close contact against the skin. In an alternative embodiment, the audio transducer 202 may be held at a distance from the skin of the patient depending on the transducer design and desired vibrational effect in the tissue to be scanned. Audio transducer 202 sends sound waves 348 into the patient which cause the target tissue 342 to undergo strain displacements (vibrate) in a manner described by Hooke's law, discussed above. While tissue 342 vibrates in response to sound waves 348, the ultrasound transducer transmits ultrasound pulses 346 and receives the reflected ultrasonic waves 344. The resulting scanned image provides an indication of various mechanical characteristics of tissue 342 revealed by the introduction of sound waves 348.

Audio Section

Figure 4:
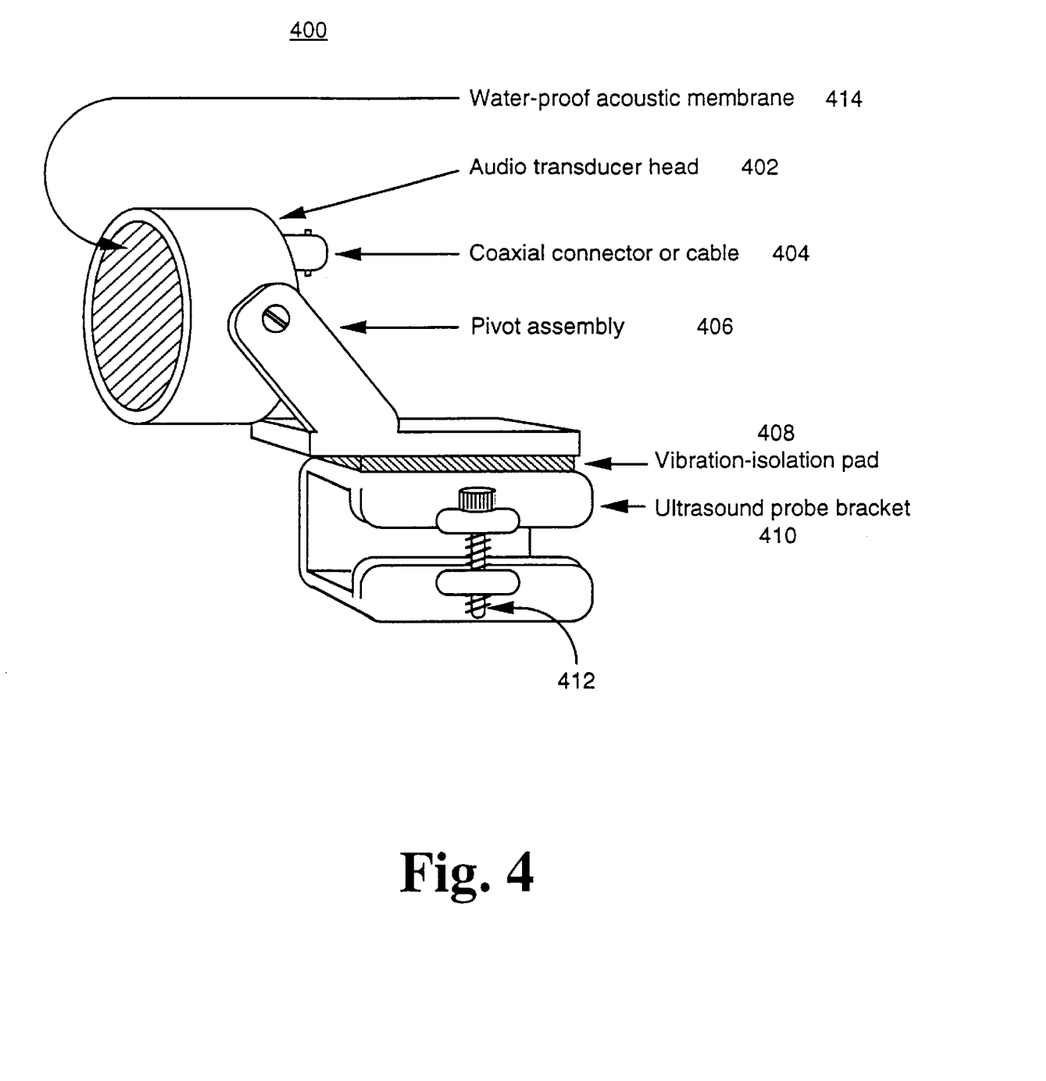
FIG. 4 illustrates an audio transducer assembly according to one embodiment of the present invention.

FIG. 4 illustrates a duplex probe arrangement according to one embodiment of the present invention, and shown as element 201 in FIG. 2. Duplex probe 400 consists of an audio-frequency transducer head 402 attached through a vibration isolation pad 408 to an ultrasound probe bracket 410. The vibration isolation pad 408 serves to mechanically isolate the two probes and prevents large-amplitude audio vibrations from interfering with the ultrasound reception in the ultrasound transducer. An acoustic membrane 414 provides the surface against which the audio transducer head 402 comes into contact with the subject's skin. Acoustic membrane 414 is made of a material which transmits sound waves, and may be made of a waterproof material to facilitate use in the presence of acoustic coupling gel and other fluids.

Ultrasound probe bracket 410 provides a structure for fixedly attaching to a standard ultrasound probe (not shown). In one embodiment of the present invention, ultrasound probe bracket 410 also includes a set screw 412 which tightens the probe within the bracket. This allows the ultrasound probe to be repositioned within the bracket, or removed from the bracket entirely if the ultrasound probe needs to be positioned in an unrestricted manner relative to the audio transducer.

In one embodiment of the present invention, audio transducer head 402 is mounted on a pivot assembly 406 which is coupled to the ultrasound probe bracket 410. The pivot assembly allows the audio transducer head to be angled relative to the ultrasound transducer and thus conform to the contour of the area of the subject being scanned. The pivot assembly thus allows the audio transducer to be brought into optimum contact with the subject's skin. A close coupling between the audio transducer head and the ultrasound probe ensures a compact dual probe assembly which facilitates ease of use and allows an operator to hold the entire assembly on the subject with only one hand.

In an alternative embodiment of the present invention, the audio transducer is coupled to the ultrasound transducer through an adjustable bracket, rather than fixed-distance bracket. The adjustable bracket may include sliding or bending members which allow the distance between the two transducers, as well as the relative angle and position between the two transducers to be freely adjusted.

In yet a further alternative embodiment of the present invention, the audio transducer and the ultrasound transducer may be held separately, with no support structure coupling the two transducers together. In this arrangement, the operator can hold the audio transducer in one hand and the ultrasound transducer in the other hand, and freely position each transducer against the subject's skin to achieve an optimum position for the introduction of the audio and ultrasound vibrations into the tissue. This allows the audio vibrations to be introduced at virtually any distance and at any angle relative to the ultrasound transducer. For example, if a patient's arm is to be scanned, this alternative arrangement allows the ultrasound probe to be held against one side of the arm, and the audio transducer to be held against the other side of the arm.

Figure 5:
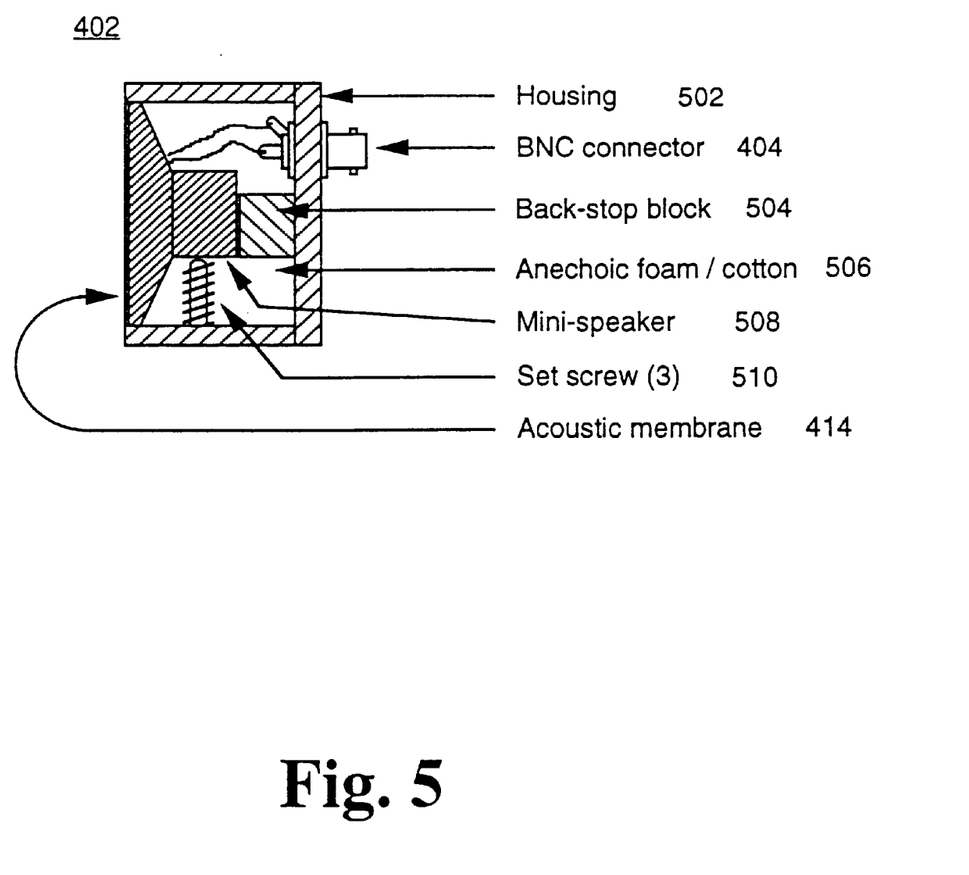
FIG. 5 illustrates an audio transducer head assembly according to one embodiment of the present invention.

FIG. 5 provides a cross-sectional illustration of the audio transducer head 402 according to one embodiment of the present invention. The audio transducer head 402 consists of an anechoic housing 502 with a waterproof skin-contact vibrational membrane 414 at one end. A locking coaxial connector 404 is provided on the back end of the audio transducer head 402. The coaxial connector provides a point of connection to an output of a signal source (e.g., audio amplifier 206 in FIG. 2). Alternatively, a coaxial cable could be provided for connection to the audio source. The coaxial connector 404 is electrically connected to an audio speaker 508 which converts the electrical signals output from the signal generator into vibrational energy. A back-stop block 504 keeps speaker 508 in place within the housing. One or more set screws 510 could be used to position and fix speaker 508 within the housing 502. The interior of housing 502 may be filled with a damping material 506, such as anechoic foam or cotton to isolate the vibrations produced by speaker 508.

The audio transducer and signal generator circuits discussed with reference to FIG. 2 were disclosed as generating signals in the audible frequency range (i.e., approximately 20 to 20 KHz). In one embodiment of the present invention, signal generators 208 or 308 are set to generate sound waves in the range of 100 Hz to 1 KHz.

In an alternative embodiment of the present invention, the audio section of the vibrational Doppler imaging system, i.e., the signal generator, amplifier, and audio transducer, produce vibrational energy outside of the audio spectrum and different from the ultrasound frequency range. In this alternative embodiment, a vibrational signal of any frequency and amplitude sufficient to cause detectable vibrations in the tissue being scanned may be produced and used, even though this signal may not be detectable by the human ear.

In a further alternative embodiment of the present invention, audio transducer 202 or 302 may be a vibrational instrument which introduces vibrations into the tissue being scanned through direct physical contact with the surface of the tissue (e.g., gentle percussive hitting or vibrating).

Ultrasound Section

In one embodiment of the present invention, the Doppler signal processing section within the vibrational Doppler imaging system 200 is a conventional color Doppler scanner with amplitude (power) Doppler imaging capability.

Figure 6:
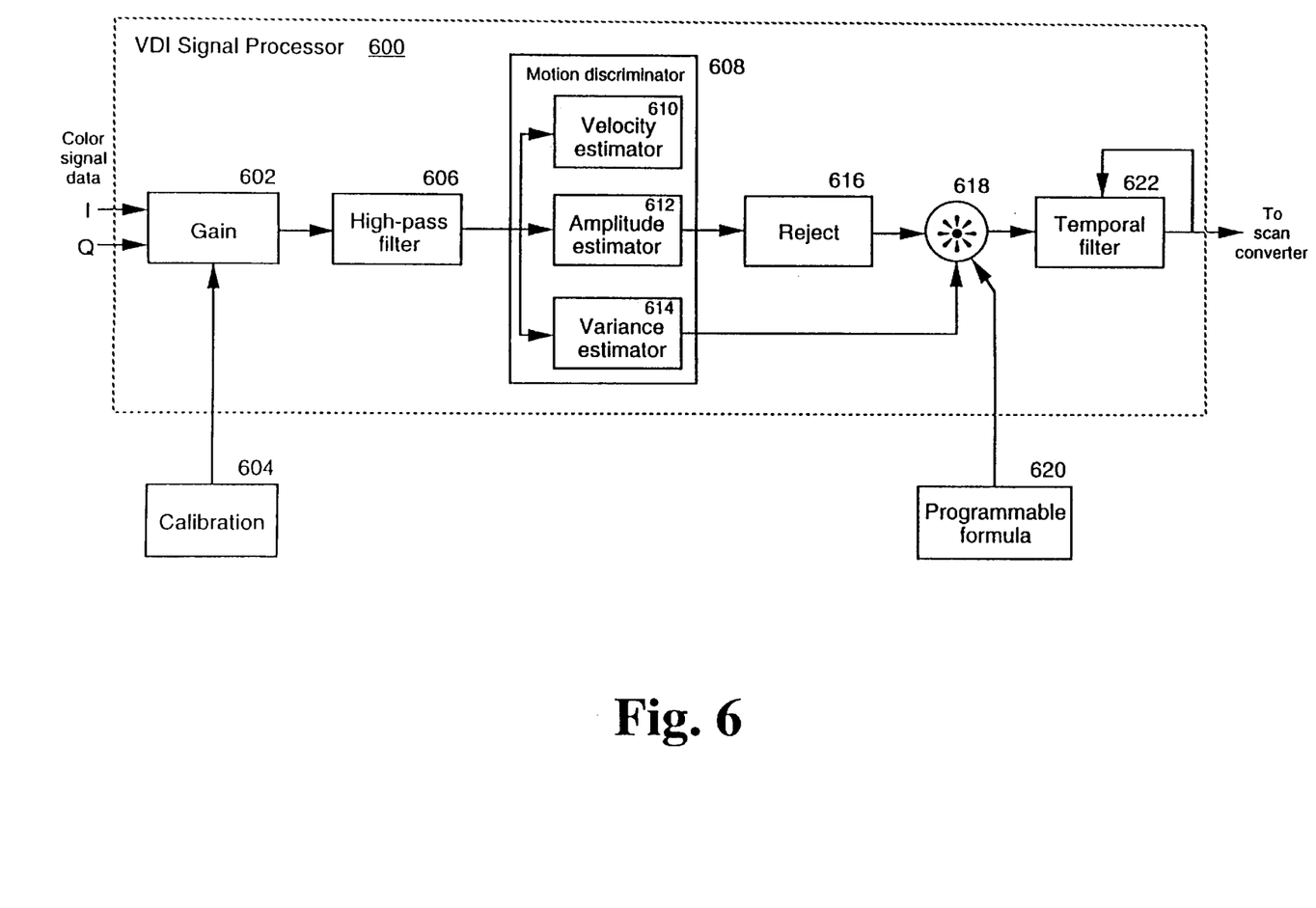
FIG. 6 is a block diagram of a Doppler signal processor for performing vibrational Doppler imaging according to one embodiment of the present invention.

In an alternative embodiment of the present invention, the Doppler signal processing section is modified to include a variance estimator and programmable arithmetic logic to operate on a combination of the amplitude and variance signals. FIG. 6 illustrates a Doppler imaging signal processing section for the vibrational Doppler imaging system according to this alternative embodiment. FIG. 6 illustrates a vibrational Doppler imaging signal processor 600 which is embodied within the color flow processor unit 104 illustrated in FIG. 1, and used in the ultrasound scanner unit 210 of FIG. 2.

The modified ultrasound system might include operator controls to use vibrational Doppler imaging as a separate imaging mode, with unique defaults for opening up the vibrational Doppler region-of-interest to cover the area of the entire B-scan image, as well as to reduce the vibrational Doppler imaging gain, and to use a gray-scale mapping of Doppler echo amplitude, and other parameters. System 600 may also include keyboard controls for audio vibration characteristics (frequency, wave shape, power), as well as on-screen displays of these parameters.

FIG. 6 is a block diagram of a digital signal processing circuit within a Doppler processor for the vibrational Doppler ultrasonic imaging system according to one embodiment of the present invention. Vibrational Doppler imaging signal processor 600 receives in-phase (I) and quadrature (Q) signals from a demodulator (e.g., RF preprocessor 103). The in-phase and quadrature signals comprise the ultrasound signal data received from the ultrasound transducer. The I/Q signals are input to a gain circuit 602. Gain circuit 602 also receives calibration signals from a calibration unit 604. Output from gain circuit 602 is input to a high pass filter 606. The output signal from the high pass filter 606 is input to a motion discriminator circuit 608.

Motion discriminator circuit 608 includes separate units that extract different parameters of motion that may be exhibited differently in different types of tissue. Motion discriminator circuit 608 includes velocity estimator 610, amplitude estimator 612, and variance estimator 614. Velocity estimator 610 extracts only the frequency shift component of the tissue motion, while amplitude estimator 612 extracts only the amplitude of the tissue motion, based on the number of reflectors. The variance estimator 614 measures the spread of velocities of the tissue motion which provides information useful in discriminating among the different types of tissue present in a scanned area.

The output from amplitude estimator 612 is input to rejection circuit 616 which acts to filter out low-level noise. The output from rejection circuit 616 is input to combinatorial circuit 618. Combinatorial circuit 618 combines the output from the rejection circuit and variance estimator 614 and processes these signals according to an operation provided by a programmable formula 620. In one embodiment of the present invention, programmable formula 620 is selected by the operator from a set of pre-programmed choices depending on the types of tissue characteristics to be detected.

The output from combinatorial circuit 618 is input into a temporal filter 622, which includes a feedback loop. Temporal filter 622 provides a time average output using a predetermined weighting factor, and serves to improve the signal-to-noise ratio of the system. The output from temporal filter 622 is also output to a scan converter (e.g., scan converter 105) which processes the signals from the Doppler processor for display on a display device (e.g., video display 212).

Figure 7:
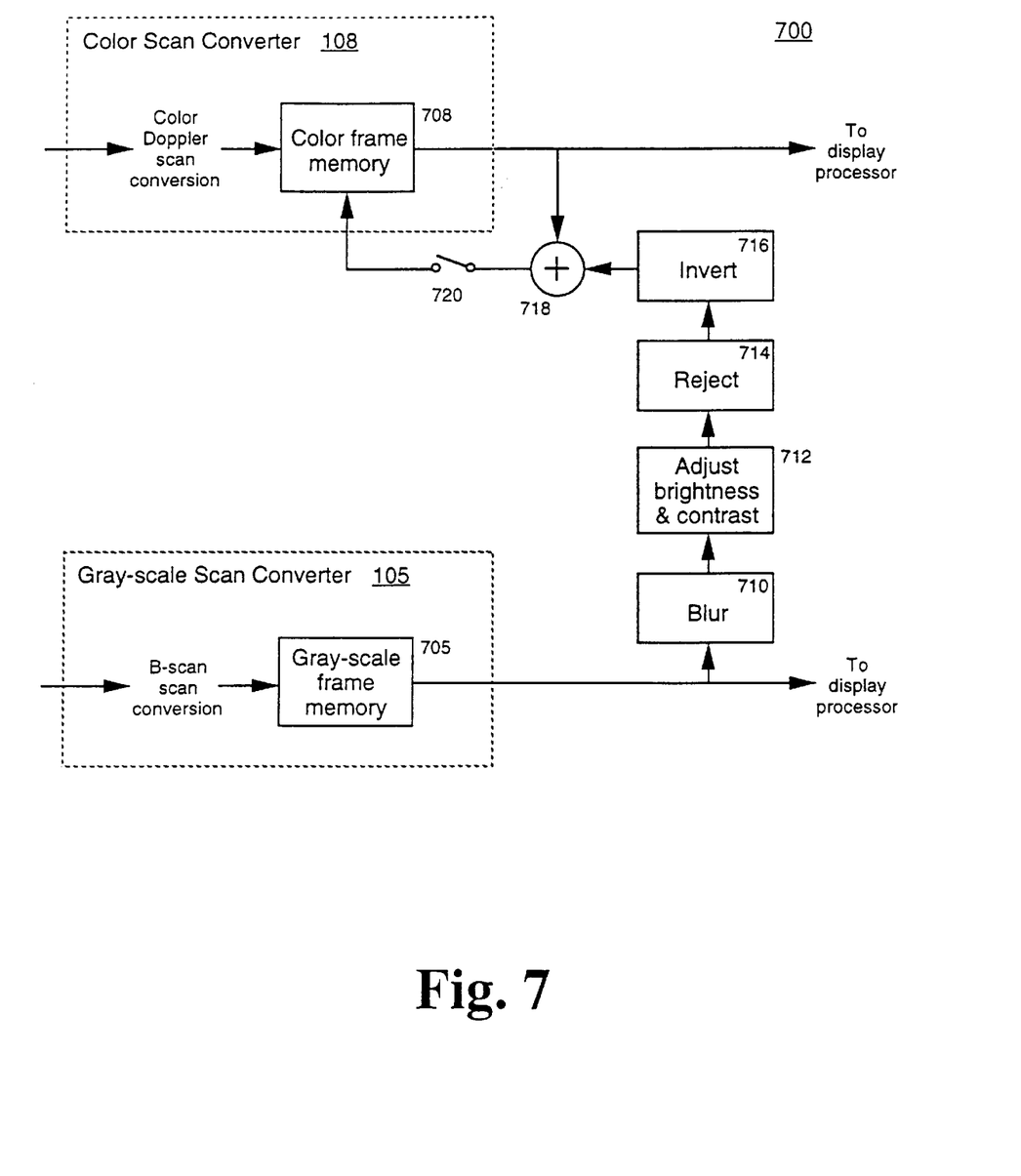
FIG. 7 is a block diagram of an echogenicity subtraction system for use in vibrational Doppler imaging according to one embodiment of the present invention.

FIG. 7 is a block diagram of an echogenicity subtraction circuit for use in vibrational Doppler imaging according to one embodiment of the present invention. As stated previously, a purely amplitude Doppler image of induced vibrations exhibits an echogenicity component in addition to the elastographic component. The echogenicity component represents the amplitude of returning ultrasound pulses and acts to distort or contaminate the information contained in the elastographic component. The echogenicity component present in embodiments of the vibrational Doppler imaging system is similar to that exhibited in conventional gray-scale B-scan ultrasonic imaging, but with lower spatial resolution.

In one embodiment of the present invention, an echogenicity subtraction element is used in vibrational Doppler imaging signal processor 600. The echogenicity subtraction element is illustrated as system 700 in FIG. 7. The function of the echogenicity subtraction system is to nullify or reduce the echogenicity component so that the elastographic component can be more clearly identified.

In one embodiment, elements comprising the echogenicity subtraction system are implemented between a standard color scan converter 108 and gray-scale scan converter 105. In gray-scale scan converter 105, B-scan converted images are stored in gray-scale frame memory 705. These images are then input through the echogenicity subtraction elements of system 700. The images are first blurred in blurring element 710. The brightness and contrast characteristics of the resulting images are then adjusted in element 712. The low-level echo components, which represent mostly noise are subtracted out in rejection element 714. The resulting image is then inverted in element 716. The image data from inverter 716 is added in adder 718 to color Doppler scan converted data processed in color scan converter 108 and stored in color frame memory 708. The added image components are input back to color frame memory 708 through switch 720. Switch 720 allows the echogenicity subtraction operation to be turned off during vibrational Doppler imaging operations. The output of both the color scan converter and gray-scale scan converter 105 are then output to a display processor (e.g., video processor 127 in FIG. 1).

Figure 8:
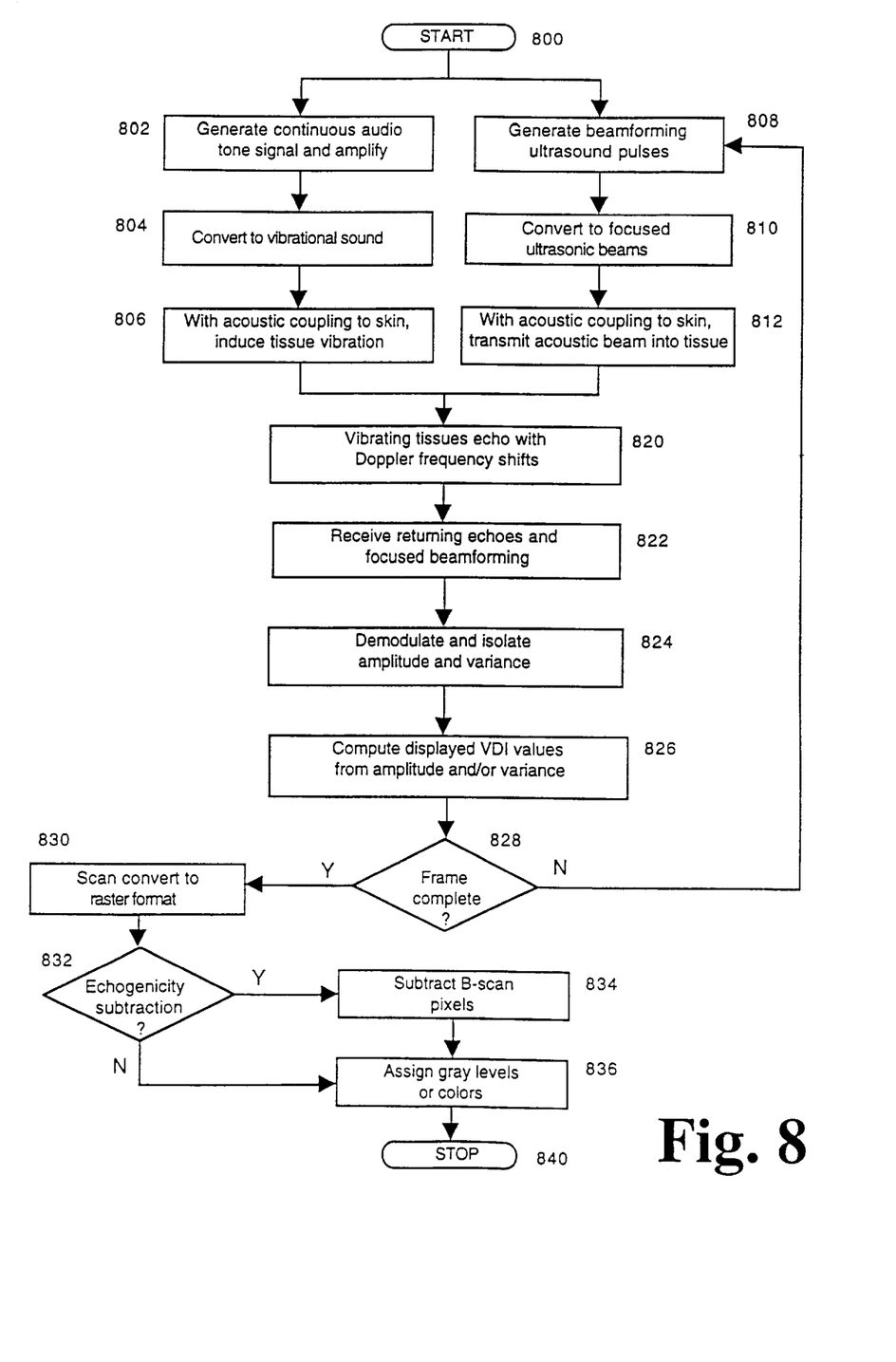
FIG. 8 is a flow chart illustrating the steps for performing vibrational Doppler ultrasound imaging according to a method of the present invention.

FIG. 8 is a flow chart illustrating the steps of performing vibrational Doppler imaging according to a method of the present invention. The flowchart in FIG. 8 illustrates the sequence of events executed by the vibrational Doppler imaging system 200 in generating Doppler image in the presence of vibrational (acoustic) signals. The basic method for this embodiment of the present invention includes the introducing an audio-frequency vibration into the area of the subject to be imaged, transmitting and receiving the ultrasonic Doppler signals into the area, and processing the resulting data for display of a two-dimensional VDI image.

The process starts at step 800 and leads into two separate and concurrent processes, one relating to formation and introduction of audio signals, and the other relating to formation and introduction of ultrasound signals. In step 802, an audio tone is generated and amplified as described in relation to the audio section of VDI system 200 illustrated in FIG. 2. The generated audio tone is converted to vibrational sound in step 804. In an embodiment of the present invention, this is performed by speaker 508 in the audio transducer 202. The vibrational sound generated in step 804 is introduced into the tissue of the subject being scanned. This step is typically performed by an operator placing the acoustic coupling membrane of the audio transducer against the skin of the subject, step 806.

Concurrently with the generation and introduction of the vibrational signals in steps 802 to 806, the ultrasound signals are generated and formed by the ultrasound section of the vibrational Doppler imaging system. In step 808, beamforming ultrasound pulses are generated. These are then converted to focused ultrasonic beams, step 810. The focused ultrasonic beams are then transmitted into the tissue of the subject being scanned, step 812. Typically this is performed by an operator placing the ultrasound transducer (probe) against the skin of the subject.

Once the audio and ultrasound signals have been generated and transmitted into this tissue of the subject being scanned, the vibrating tissues echo with Doppler frequency shifts in accordance with the frequency at which the ultrasound and audio tones were generated, step 820. The vibrational Doppler imaging system then receives the returning ultrasound echoes, step 822. These signals are then demodulated and the amplitude and variance portions are isolated, step 824. In step 826, the system computes the displayed VDI values from the amplitude and/or variance portions isolated in step 824. In one embodiment of the present invention, this computation is performed by combinatorial circuit 618 using the combinatorial formula provided by the programmed formula element 620 in FIG. 6.

Once the computation of the VDI values is performed, the system determines whether the imaging frame is complete, step 828. If it is determined that the frame is not complete, another vector is obtained by repeating steps 808 to 826. That is, the process starts from the generation of the beam forming ultrasound pulses, step 808. It should be noted that the generation and introduction of audio tones, steps 802 to 806 is a continuous process, so the process of getting another vector needs only to re-start from the generation of the ultrasound signal in step 808.

If, however, in step 828 it is determined that the frame is complete, the frame is scan converted to raster format, step 830. In step 832 it is determined if an echogenicity subtraction operation is to be performed. In one embodiment of the present invention, this is determined by determining the position of switch 720 in echogenicity subtraction system 700. If echogenicity subtraction is to be performed, B-scan pixels are subtracted from the frame, step 834. After subtraction of B-scan pixels, the resulting frame is assigned gray-scale levels or colors for display on a display device, step 836, and the process ends, step 840. If, however, in step 832, it is determined that echogenicity subtraction is not to be performed on the frame, no B-scan pixels are subtracted and the frame is assigned gray-scale levels or colors directly in step 836. At this point the process ends, step 840.

In the foregoing, a system has been described for Doppler-based ultrasound imaging using audio-frequency vibrations introduced into the tissue being imaged. Although the present invention has been described with reference to specific exemplary embodiments, it will be evident that various modifications and changes may be made to these embodiments without departing from the broader spirit and scope of the invention as set forth in the claims. Accordingly, the specification and drawings are to be regarded in an illustrative rather than a restrictive sense.

What is claimed is:

1. An ultrasonic imaging apparatus comprising:
    a first transducer, said first transducer operable to transmit vibrational energy of a first frequency within a first frequency range into an area of a subject to be scanned;
    a second transducer coupled to said first transducer, said second transducer operable to transmit sound energy of a second frequency within a second frequency range into said area, said second frequency range including an ultrasonic frequency range; and
    a variable frequency signal generator coupled to said first transducer, said variable frequency generator operable to generate waveforms within said first frequency range to be transmitted by said first transducer; and wherein said first transducer causes a medium within said area to vibrate at a frequency related to said first frequency.

2. An apparatus according to claim 1 wherein said first frequency range includes an audio frequency range and said first transducer comprises an audio transducer contained within a housing.

3. An apparatus according to claim 2 wherein said second transducer comprises an ultrasound probe, and said second transducer is coupled to an ultrasound scanner, said ultrasound scanner comprising:
    an ultrasound imaging circuit operable to receive ultrasound data from said second transducer and producing ultrasound Doppler image data; and
    an ultrasound processor unit operable to process said ultrasound Doppler image data for display on a display device coupled to said ultrasound scanner.

4. An apparatus according to claim 3 wherein said ultrasound scanner includes a host processor, said host processor configured to provide an operator interface and to control said variable frequency signal generator in accordance with commands entered by an operator through said operator interface.

5. An apparatus according to claim 2 wherein said first transducer is coupled to said second transducer through a pivotable bracket assembly, said pivotable bracket assembly comprising:
    a first bracket operable to hold said first transducer; and
    a second bracket operable to hold said second transducer and coupled to said first bracket, wherein said first bracket is operable to hold said first transducer through a pivot connection which allows said first transducer to be positioned against a surface at an angle relative to said second transducer.

6. An apparatus according to claim 5 wherein said first bracket is coupled to said second bracket through a vibration isolation pad.

7. An apparatus according to claim 6 wherein said first transducer comprises a waterproof membrane connected to an opening of said housing, said membrane providing a skin contact surface for said audio transducer, said membrane being made of a material which allows transmission of audio waves therethrough.

8. An apparatus according to claim 3 wherein said ultrasound processing unit includes a motion discriminator circuit, said motion discriminator circuit comprising:
    an amplitude estimator circuit configured to extract amplitude information from said ultrasound Doppler image data;
    a velocity estimator circuit configured to extract frequency shift information from said ultrasound Doppler image data; and
    a variance estimator circuit configured to extract frequency shift distribution information from said ultrasound Doppler image data.

9. An apparatus according to claim 8 wherein said ultrasound processing unit further comprises a combinatorial circuit coupled to said motion discriminator circuit, said combinatorial circuit configured to accept as input data output values from said amplitude estimator circuit and said variance estimator circuit, and combine said input data in accordance with a formula programmed into said ultrasound processing unit.

10. An apparatus according to claim 2 wherein said audio transducer is a speaker, and said first frequency is within the range of 100 Hz to 1000 Hz.

11. An apparatus according to claim 3 further comprising an echogenicity subtraction circuit within said ultrasound processor unit, said echogenicity subtraction circuit operable to reduce an echogenicity component within said ultrasound Doppler image data.

12. An apparatus according to claim 11 wherein said echogenicity subtraction circuit is coupled between a gray-scale scan converter and a color scan converter within said ultrasonic imaging apparatus, said echogenicity subtraction circuit comprising:
    a blurring circuit coupled to said gray-scale scan converter;
    an image adjustment circuit coupled to said blurring circuit;
    a rejection circuit coupled to said adjustment circuit, said rejection circuit operable to subtract a noise component from an image processed by said gray-scale scan converter;
    an inverter circuit coupled to said rejection circuit; and
    an adder circuit coupled between said color scan converter and said inverter.

13. An method of performing ultrasonic imaging comprising the steps of:
   (a) generating and amplifying a first signal of a first frequency;
   (b) converting said first signal into vibrational energy;
   (c) introducing said first signal into an area a subject to be ultrasonically imaged;
   (d) generating beamforming ultrasound pulses;
   (e) converting said beamforming ultrasound pulses into focused ultrasonic beams; and
   (f) introducing said focused ultrasonic beams into said area.

14. A method according to claim 13 wherein steps (a) through (c) are performed concurrently with steps (d) through (f).

15. A method according to claim 14 wherein said first frequency is within an audio frequency range, and said step of introducing said first signal into said area causes tissue medium within said area to vibrate at a frequency related to said first frequency.

16. A method according to claim 15 wherein
   said first signal is introduced into said area through an audio transducer coupled to a variable frequency tone generator; and
   said focused ultrasonic beams are introduced into said area through an ultrasonic probe coupled to an ultrasonic Doppler imaging system.

17. A method according to claim 16 further comprising the steps of:
   (g) receiving returning echoes and focused ultrasonic beams from said area;
   (h) demodulating and isolating amplitude and variance information from said received signals;
   (i) computing Doppler imaging values from said amplitude and variance information in accordance with a pre-determined relationship;
   (j) scan converting said Doppler imaging values for complete frames into a raster format; and
   (i) assigning gray-scale or color values to said Doppler imaging values for display on a display device.

18. A method according to claim 16 wherein said audio transducer is a speaker, and said first frequency is within the range of 100 Hz to 1000 Hz.

19. An apparatus comprising:
   first transducer means for transmitting energy of a first frequency within a first frequency range into an area of a subject to be scanned; and
   second transducer means for transmitting energy of a second frequency within a second frequency range into said area, said second frequency range including an ultrasonic frequency range, said second transducer means coupled to said first transducer means;
   signal generator means for generating waveforms within said first frequency range to be transmitted by said first transducer means, said signal generator means coupled to said first transducer means.

20. An apparatus according to claim 19 further comprising ultrasonic Doppler imaging means for generating and processing ultrasonic imaging data transmitted and received by said second transducer means.

21. An apparatus according to claim 20 further comprising bracket means for holding said first transducer means and said second transducer means such that said first transducer and said second transducer can be held proximately in contact with said area, and further such that the respective angle of contact between said first and said second transducer means against a surface of said area can be adjusted.

22. An apparatus according to claim 21 wherein said ultrasonic Doppler imaging means includes processing means, said processing means operable to provide a user interface and to control said signal generator means in accordance with commands entered by an operator through said user interface.

* * * * *